United States Patent [19]

Lachhein et al.

[11] Patent Number: 5,155,222
[45] Date of Patent: Oct. 13, 1992

[54] PROCESS FOR THE PREPARATION OF N-ALKYLSULFONYLAMINOSULFONYLUREAS

[75] Inventors: Stephen Lachhein, Hofheim am Taunus; Lothar Willms, Hillscheid, both of Fed. Rep. of Germany

[73] Assignee: Hoechst Aktiengesellschaft, Frankfurt am Main, Fed. Rep. of Germany

[21] Appl. No.: 731,518

[22] Filed: Jul. 17, 1991

[30] Foreign Application Priority Data

Jul. 19, 1990 [DE] Fed. Rep. of Germany ....... 4022982

[51] Int. Cl.⁵ ............... C07D 239/42; C07D 239/48
[52] U.S. Cl. .................................. 544/332; 544/323; 544/320; 544/321
[58] Field of Search ............... 544/320, 321, 323, 332

[56] References Cited

U.S. PATENT DOCUMENTS 4,534,790 8/1985 Wolf ..................................... 71/93

OTHER PUBLICATIONS

"Advanced Organic Chemistry", Mar., p. 444 (1985) John Wiley & Sons, New York.
Paquin, *Angew Chem*, vol. 60, pp. 316, 317 and 319 (1948).
Preiss, *Chem. Ber.*, vol. 111, pp. 1915, 1916, 1918–1919 (1978).
Arya, *Indian J. Chem.*, vol. 21B, pp. 941, 943 & 944 (1982).

*Primary Examiner*—John M. Ford
*Attorney, Agent, or Firm*—Curtis, Morris & Safford

[57] ABSTRACT

Known herbicides of the formula (I)

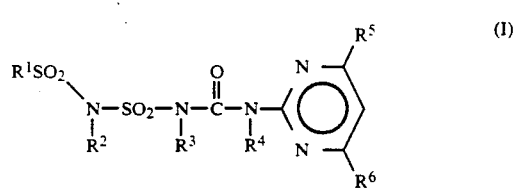

in which
 $R^1$ is alkyl, alkenyl or alkynyl, which are optionally substituted by halogen, alkoxy or alkoxycarbonyl,
 $R^2$ is H, alkyl, alkenyl, alkynyl or cycloalkyl,
 $R^3$ and $R^4$ are H or alkyl,
 $R^5$ and $R^6$ are H, alkyl or alkoxy, each of which can be substituted by halogen, alkoxy or alkylthio, or are halogen, alkylthio, alkylamino or dialkylamino, or, if $R^2$ or $R^3$ is H, their salts with bases, can be obtained when compounds of the formula II $$R^1\text{-}SO_2\text{-}NR^2\text{-}SO_2\text{-}NHR^3 \quad \text{(II)}$$

in which
 $R^1$, $R^2$ and $R^3$ are as defined above,
are reacted with compounds of the formula III

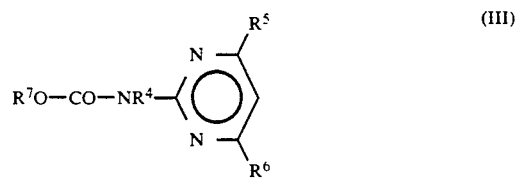

in which
 $R^4$, $R^5$ and $R^6$ are as defined above and
 $R^7$ is alkyl, haloalkyl or optionally substituted phenyl,
in an inert organic solvent, to give the compounds of the formula I.

20 Claims, No Drawings

PROCESS FOR THE PREPARATION OF N-ALKYLSULFONYLAMINOSULFONYLUREAS

The present invention relates to a process for the preparation of the compounds of the formula I

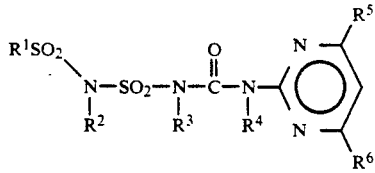

in which
R$^1$ is (C$_1$-C$_6$)-alkyl, (C$_2$-C$_6$)-alkenyl or (C$_2$-C$_6$)-alkenyl, each of the 3 radicals mentioned being unsubstituted or mono- or polysubstituted by radicals from the group comprising halogen, (C$_1$-C$_4$)-alkoxy and [(C$_1$-C$_4$)-alkoxy]carbonyl,
is hydrogen, (C$_1$-C$_6$)-alkyl, (C$_2$-C$_6$)-alkenyl, (C$_2$-C$_6$)-alkynyl or (C$_3$-C$_6$)-cycloalkyl,
R$^3$ and R$^4$ independently of one another are hydrogen or (C$_1$-C$_4$)-alkyl,
R$^5$ and R$^6$ independently of one another are hydrogen or (C$_1$-C$_4$)-alkyl,
R$^5$ and R$^6$ independently of one another are hydrogen, (C$_1$-C$_4$)-alkyl or (C$_1$-C$_4$)-alkoxy, the 2 last-mentioned radicals being unsubstituted or mono- or polysubstituted by radicals from the group comprising halogen, alkoxy and alkylthio, or are halogen, (C$_1$-C$_4$)-alkylthio, (C$_1$-C$_4$)-alkylamino or (C$_1$-C$_4$)-dialkylamino,
and, if R$^2$ and R$^3$ are hydrogen, their physiologically acceptable salts with bases.

Compounds of the formula I are known and are employed as plant protection agents having a herbicidal action; see, for example, EP-A 0,131,258.

This publication also already refers to, or describes, a range of processes by which compounds of the formula I can be prepared.

The disadvantage of the known processes is the relatively low yields of not more than 65-70%. As a consequence of these low yields, considerable amounts of contamination and by-products are produced. From an ecological as well as an economical point of view, these described processes cannot be carried out on a large scale, since the large amounts of by-products and waste which would result thereby are unacceptable, and their disposal, for example by incineration, is complicated. Moreover, such low yield means that the loss of starting materials employed is drastic.

A novel process has now been found by which the compounds of the formula I can be prepared in a surprisingly high yield and purity.

The process according to the invention comprises reacting compounds of the formula II $$R^1-SO_2-NR^2-SO_2NHR^3 \quad (II)$$

in which
R$^1$, R$^2$ and R$^3$ are as defined above,
with compounds of the formula III

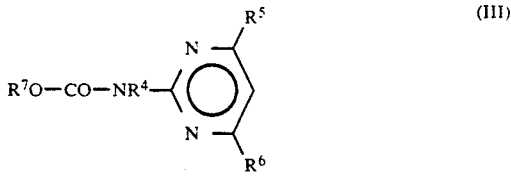

in which
R$^4$, R$^5$ and R$^6$ are as defined above and
R$^7$ is alkyl, haloalkyl or optionally substituted phenyl,
in an inert organic solvent, to give the compounds of the formula I.

In the formulae mentioned and in the following text, alkyl, alkoxy, haloalkyl, alkylamino and alkylthio radicals as well as the corresponding unsaturated and/or substituted radicals can, unless otherwise indicated, in each case be straight-chain or branched as far as the carbon chain is concerned; alkyl radicals, also in the compound meanings such as alkoxy, haloalkyl, etc., are, for example, methyl, ethyl, n- or i-propyl, n-, i-, t- or 2-butyl; alkenyl and alkynyl radicals have the meaning of the possible unsaturated radicals which correspond to the alkyl radicals, such as 2-propenyl, 2- or 3-butenyl, 2-propynyl, 2- or 3-butynyl; optionally substituted phenyl is, for example, phenyl which is unsubstituted or substituted by one or more, preferably 1 to 3, radicals from the group comprising halogen, C$_1$-C$_4$)-alkyl, (C$_1$-C$_4$)-alkoxy, (C$_1$-C$_4$)-haloalkyl, (C$_1$-C$_4$)-thioalkyl, (C$_1$-C$_4$-alkoxy)carbonyl, (C$_1$-C$_4$-alkyl)sulfonyl, cyano and nitro; halogen, also halo in haloalkyl etc., is fluorine, chlorine, bromine or iodine, preferably fluorine, chlorine or bromine.

Preferred processes amongst the processes according to the invention for the preparation of the compounds of the formula I are those in which R$^1$ and R$^2$ independently of one another are (C$_1$-C$_3$)-alkyl or (C$_1$-C$_3$)-alkenyl, in particular (C$_1$-C$_2$)-alkyl, R$^3$ and R$^4$ are hydrogen, R$^5$ and R$^6$ independently of one another are (C$_1$-C$_2$)-alkyl or (C$_1$-C$_2$)-alkoxy, in particular methyl or methoxy.
R$^7$ is preferably (C$_1$-C$_4$)-alkyl, (C$_1$-C$_4$)-haloalkyl or phenyl, in particular ethyl or phenyl.

As a rule, the yields in the process according to the invention are at least 95% of theory, and the purities of the sulfonylureas I formed are usually higher than 98% by weight.

The process according to the invention is carried out in inert organic solvents. Examples of types of solvents in this context are aromatic, optionally halogenated hydrocarbons and aprotic polar solvents such as dialkylalkanoylamides, dialkyl sulfoxides, polyalkylene glycol dialkyl ethers, N-alkylated cyclic amides and nitriles. Examples of preferred solvents are toluene, xylene, chlorobenzene, dimethylformamide, dimethyl sulfoxide, di-, tri- or tetraethylene glycol dialkyl ethers, in particular di-, tri- or tetraethylene glycol dimethyl ether or di-, tri- or tetraethylene glycol diethyl ether, N-methylpyrrolidone, acetonitrile, and also mixtures of two or more of the solvents mentioned.

As a rule, the ratio of the compound of the formula II to the compound of the formula III is equimolar or the former is employed in a slight excess. A preferred molar ratio of II:III is from 1:1 to 1.2:1, in particular 1:1 to 1.1:1.

It is an advantage of the process according to the invention that the solvent can be recycled in virtually quantitative yield because the product of the formula I precipitates from the reaction medium in the form of a sparingly soluble compound in high purity and yield. The solvent can then be purified, for example by distillation, and fed back into the production process.

The reaction temperatures range preferably from 0° C. to the boiling point of the solvent employed, in particular from room temperature (for example 20° C.) to 110° C.

The starting compounds of the formulae II and III which are required for the preparation of the compounds according to the invention of the general formula I can be synthesized by processes known from the literature.

For example, the compounds of the formula II are obtained analogously to conventional methods (see, for example, "Organikum", 7th edition, p. 359, VEB Deutscher Verlag der Wissenschaften, Berlin 1967) by reacting the corresponding sulfonamides IV with sulfamoyl chlorides V.

The compounds of the formula III are obtained in high yields from the corresponding heterocycles VI by customary laboratory methods (see, for example, Tietze und Eicher in "Reaktionen und Synthesen" [Reactions and Syntheses] p. 92, Thieme Vrlag, Stuttgart 1981) by reacting them with chloroformic esters VII:

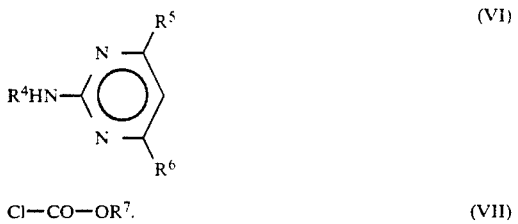

The heterocycles of the formula VI are either commercially available or can be prepared easily following suitable customary methods; see, for example, U.S. Pat. No. 4,310,470; EP 0,024,200; U.S. Pat. No. 4,299,960; M. J. Langerman, C. K. Banks, J. Am. Chem. Soc. 73, 3011 (1951).

The process can be carried out batchwise or continuously.

The process according to the invention must be regarded as particularly surprising because the starting materials of the formulae II and III contain a plurality of activated electrophilic and nucleophilic centers, all of which could, in principle, react with nucleophilic and electrophilic moieties of molecules and in this way could give a large number of by-products because of fragmentation reactions. The compounds of the formula II have, in particular, two sulfonyl groups as virtually equivalent leaving groups; sulfonyl groups are very good leaving groups (cf. Beyer, Lehrbuch der organischen Chemie [Textbook of Organic Chemistry], 19th edition, p. 128, Hirzel Verlag Stuttgart). Surprisingly, the process according to the invention avoids by-products virtually completely.

The process according to the invention therefore represents a process for synthesizing the compounds of the formula I in virtually quantitative yields which is novel and simple, and readily reproducible and highly selective, even on a larger, industrial scale.

In the following text, the process according to the invention will be illustrated with the aid of a number of examples. Unless otherwise indicated, percentages are by weight.

EXAMPLE 1

1-[(N-Methylsulfonyl-N-methylamino)sulfonyl]-3-(4,6-dimethoxy-2-pyrimidyl)urea 37.6 g of (N-methylsulfonyl-N-methylamino)sulfonamide are dissolved in 500 ml of acetonitrile, 55.0 g of phenyl 4,6-dimethoxy-2-pyrimidylcarbamate are added dropwise at room temperature, and the mixture is stirred for 18 hours at room temperature. Approx. 400 ml of acetonitrile are distilled off, and then 200 ml of water are added at 0° C., and the mixture is brought to pH 2-3 using 2N HCl. The product which has precipitated is filtered off with suction and washed with water. 72.6 g of the desired product of a purity of 98.4% are obtained, which corresponds to a yield of 96.8% of theory. The melting point of the product is 185-186° C.

EXAMPLE 2

1-[(N-Methylsulfonyl-N-methylamino)sulfonyl]-3-(4-methoxy-6-methyl-2-pyrimidyl)urea 37.6 g of (N-methylsulfonyl-N-methylamino)sulfonamide are dissolved in 500 ml of chlorobenzene, 51.8 g of phenyl 4-methoxy-6-methyl-2-pyrimidylcarbamate are added dropwise at room temperature to the solution, and the mixture is stirred for 5 hours at 100° C. The mixture is cooled to 0° C., the precipitate is then filtered off, and, after washing with 100 ml of chlorobenzene, 68.8 g of the desired product of a purity of 98.7% are obtained. This corresponds to a yield of 96.4% of theory. The melting point of the product is 118-120° C.

EXAMPLE 3

1-[(N-Ethylsulfonyl-N-ethylamino)sulfonyl]-3-(4,6-diethoxy-2-pyrimidyl)urea 40.4 g of (N-ethylsulfonyl-N-methylamino)sulfonamide are dissolved in 500 ml of toluene, and 51.0 g of ethyl 4,6-dimethoxy-2-pyrimidylcarbamate are added dropwise at 100° C. with stirring. After a reaction time of 3 hours at 100° C., the mixture is cooled to 0° C., and the precipitate is filtered off. After washing with 100 ml of toluene, 83.0 g of the desired product of a purity of 98.0% are obtained, which corresponds to a yield of 95.7% of theory. The melting point of the product is 175-176° C.

The compounds of the formula I which are listed in Table 1 below are synthesized analogously to Examples 1 to 3.

TABLE 1

| Ex. No. | $R^1$ | $R^2$ | $R^3$ | $R^4$ | $R^5$ | $R^6$ | M.p. (°C.) |
|---|---|---|---|---|---|---|---|
| 4 | $CH_3$ | $CH_3$ | H | H | $CH_3$ | $CH_3$ | 150-151 |
| 5 | $CH_3$ | $C_3H_7$ | H | H | $CH_3$ | $CH_3$ | 149-151 |
| 6 | $CH_3$ | $C_3H_7$ | H | H | $OCH_3$ | $CH_3$ | 141-143 |
| 7 | $CH_3$ | $CH_2=CHCH_2$ | H | H | $CH_3$ | $CH_3$ | 139-141 |
| 8 | $CH_3$ | $CH_2=CHCH_2$ | H | H | $OCH_3$ | $CH_3$ | 159-161 |

TABLE 1-continued

| Ex. No. | R¹ | R² | R³ | R⁴ | R⁵ | R⁶ | M.p. (°C.) |
|---|---|---|---|---|---|---|---|
| 9 | $CH_2Cl$ | $CH_3$ | H | H | $CH_3$ | $CH_3$ | 146–148 |
| 10 | $CH_3$ | $C_3H_7$ | H | H | $OCH_3$ | $OCH_3$ | 156–157 |
| 11 | $CH_3$ | $CH(CH_3)_2$ | H | H | $OCH_3$ | $OCH_3$ | 121–123 |
| 12 | $CH_3$ | $CH(CH_3)_2$ | H | H | Cl | $OCH_3$ | 153–155 |
| 13 | $C_2H_5$ | $C_2H_5$ | H | H | $OCH_3$ | $OCH_3$ | |
| 14 | $CH_3$ | $CH_3$ | $CH_3$ | H | $OCH_3$ | $OC_2H_5$ | |
| 15 | $CH_3$ | $CH_3$ | H | $CH_3$ | $OCH_3$ | $OCH_3$ | |
| 16 | $CH_3$ | $C_2H_5$ | $CH_3$ | $CH_3$ | $C_2H_5$ | $OCH_3$ | |
| 17 | $C_3H_7$ | $CH_3$ | H | H | $CH_3$ | $CH_3$ | |
| 18 | $C_4H_9$ | $CH_3$ | H | H | $OCH_3$ | $OCH_3$ | |
| 19 | $CH_3$ | cyclo-$C_6H_{11}$ | H | H | $OCH_3$ | $OCH_3$ | |
| 20 | $CH_3$ | $CH_2-C\equiv CH$ | $CH_3$ | H | $CH_3$ | $OCF_2H$ | |
| 21 | $CH_3$ | $CH_2-CO_2CH_3$ | H | H | $CH_3$ | $CH_3$ | |

We claim:

1. A process for the preparation of the compounds of the formula I

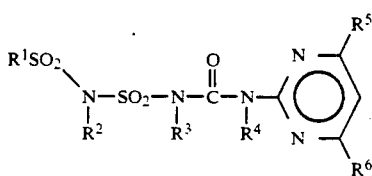

in which

R¹ is $(C_1-C_6)$-alkyl, $(C_2-C_6)$-alkenyl or $(C_2-C_6)$-alkynyl, each of the 3 radicals mentioned being unsubstituted or mono- or polysubstituted by halogen, $(C_1-C_4)$-alkoxy and $[(C_1-C_4)$-alkoxy]-carbonyl, R² is hydrogen, $(C_1-C_6)$-alkyl, $(C_2-C_6)$-alkenyl, $(C_2-C_6)$-cycloalkyl, R³ and R⁵ independently of one another are hydrogen or $(C_1-C_4)$-alkyl, R⁵ and R⁶ independently of one another are hydrogen, $(C_1-C_4)$-alkyl or $(C_1-C_4)$-alkoxy, the 2 last-mentioned radicals being unsubstituted or mono- or polysubstituted by radicals from the group comprising halogen, alkoxy and alkylthio, or are halogen, $(C_1-C_4)$-alkylthio, $(C_1-C_4)$-alkylamino or $(C_1-C_4)$-dialkylamino, and, if R² and R³ are hydrogen, their physiologically acceptable salts with bases, which comprises reacting compounds of the formula II

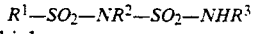

in which

R¹, R² and R³ are as defined above, with compounds of the formula III

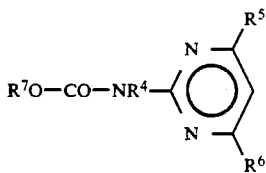

in which

R⁴, R⁵ and R⁶ are as defined above, R⁷ is alkyl, haloalkyl or optionally substituted phenyl, in an inert organic solvent, to give the compounds of the formula I.

2. The process as claimed in claim 1, in which R¹ and R² independently of one another are $C_1-C_3$)-alkyl or $C_1-C_3$)-alkenyl, R³ and R⁴ are hydrogen, and R⁵ and R⁶ independently of one another are $(C_1-C_2)$-alkyl or $(C_1-C_2)$-alkoxy.

3. The process as claimed in claim 1, in which R¹ is $(C_1-C_2)$-alkyl, R² is $(C_1-C_3)$-alkyl or $(C_1-C_3)$-alkenyl, R³ and R⁴ are hydrogen, R⁵ is methyl or methoxy and R⁶ is methyl or methoxy.

4. The process as claimed in claim 1, in which R⁷ is $(C_1-C_4)$-alkyl, $(C_1-C_4)$-haloalkyl or phenyl.

5. The process as claimed in claim 1, wherein the inert organic solvents employed are aromatic hydrocarbons, halogenated aromatic hydrocarbons or aprotic polar solvents, or mixtures of the solvents mentioned.

6. The process as claimed in claim 1, wherein the temperatures at which the reaction is carried out are from 0° C. to the boiling point of the solvent employed.

7. The process as claimed in claim 6, wherein the reaction temperature ranges from room temperature up to 110° C.

8. The process as claimed in claim 1, wherein the compounds II and III are reacted in a molar ratio of 1:1 to 1.2:1.

9. The process as claimed in claim 8, wherein the molar ratio is 1:1 to 1.1:1.

10. The process as claimed in claim 1, wherein the process is carried out batchwise or continuously.

11. The process as claimed in claim 5, wherein the reaction temperature is from 0° C. to the boiling point of the solvent employed.

12. The process as claimed in claim 11, wherein the compounds of formulae II and III are reacted in a molar ratio of 1:1 to 1.2:1.

13. The process as claimed in claim 12, wherein the reaction temperature is from room temperature to 110° C.

14. The process as claimed in claim 13, wherein the compounds of formulae II and III are reacted in a molar ratio of 1:1 to 1.1:1.

15. The process as claimed in claim 1, wherein R¹ is methyl or ethyl, R² is methyl or ethyl, R³ is hydrogen, R⁴ is hydrogen, R⁵ is methyl, ethyl, methoxy or ethoxy, R⁶ is methyl, ethyl, methoxy or ethoxy and R⁷ is methyl or phenyl.

16. The process as claimed in claim 15, wherein R¹ is methyl, R² is methyl, R⁵ is methoxy and R⁶ is methoxy.

17. The process as claimed in claim 15, wherein R¹ if methyl, R² is methyl, R⁵ is methyl and R⁶ is methyl.

18. The process as claimed in claim 15, wherein R¹ is methyl, R² is methyl, R⁵ is methoxy and R⁶ is methyl.

19. The process as claimed in claim 15, wherein the solvent is selected from the group consisting of aromatic hydrocarbons, halogenated hydrocarbons and aprotic polar solvents; the reaction temperature is from 20° C. to 110° C.; and compounds II and III are reacted in a molar ration of 1:1 to 1.2:1.

20. The process as claimed in claim 15, wherein the solvent is selected from the group consisting of chlorobenzene, toluene and acetonitrile; and compounds II and III are reacted in a molar ration of 1:1 to 1.1:1.

* * * * *